(12) United States Patent
Bajramovic et al.

(10) Patent No.: US 9,259,148 B2
(45) Date of Patent: Feb. 16, 2016

(54) METHOD FOR MEASURING AN EYE

(71) Applicant: Carl Zeiss Meditec AG, Jena (DE)

(72) Inventors: Ferid Bajramovic, Jena (DE); Ralf Ebersbach, Schmoelln (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 13/962,652

(22) Filed: Aug. 8, 2013

(65) Prior Publication Data
US 2014/0049753 A1 Feb. 20, 2014

(30) Foreign Application Priority Data

Aug. 16, 2012 (DE) .......... 10 2012 016 379

(51) Int. Cl.
*A61B 3/00* (2006.01)
*A61B 3/10* (2006.01)
*A61B 3/14* (2006.01)

(52) U.S. Cl.
CPC .............. *A61B 3/1005* (2013.01); *A61B 3/102* (2013.01)

(58) Field of Classification Search
CPC .......... A61B 3/103; A61B 3/14; A61B 3/152; A61B 3/113; A61B 3/1225; A61B 3/024; A61B 3/032; A61B 3/1015; A61B 3/107
USPC ......... 351/247, 246, 200, 205–206, 208–210, 351/221–223
See application file for complete search history.

(56) References Cited

U.S. PATENT DOCUMENTS

| | | | |
|---|---|---|---|
| 5,321,501 A | 6/1994 | Swanson et al. | |
| 6,116,738 A * | 9/2000 | Rorabaugh | 351/247 |
| 7,452,077 B2 | 11/2008 | Meyer et al. | |
| 2002/0044258 A1 * | 4/2002 | Sarver et al. | 351/212 |
| 2008/0055543 A1 | 3/2008 | Meyer et al. | |
| 2009/0326650 A1 * | 12/2009 | Zickler et al. | 623/5.11 |
| 2011/0157554 A1 * | 6/2011 | Kawai et al. | 351/221 |
| 2012/0184846 A1 | 7/2012 | Izatt et al. | |

(Continued)

FOREIGN PATENT DOCUMENTS

| | | |
|---|---|---|
| DE | 198 52 331 A1 | 5/2000 |
| DE | 10 2010 046 500 A1 | 3/2012 |
| DE | 10 2010 051 281 A1 | 5/2012 |

OTHER PUBLICATIONS

Haigis, "Optical Coherence Biometry", Modern Cataract Surgery, T. Kohnen, Ed. Basel: Karger Publishers, 2002, pp. 119-130.

(Continued)

*Primary Examiner* — Dawayne A Pinkney
(74) *Attorney, Agent, or Firm* — Patterson Thuente Pedersen, P.A.

(57) ABSTRACT

A method for measuring the axial length of an eye using optical coherence tomography, during which a plurality of A-scans of the OCT measurement are combined to an axial length, taking into account the alignment with which they were obtained, and taking into account the topography of the cornea. The distance of the front of the cornea from the retina is determined using OCT while measuring or controlling the alignment of the measuring device to the eye in that the topography of the front of the cornea is measured or made available. The calculation of an axial length from an A-scan of the OCT takes into account a corneal topography registered to the A-scans and is the basis for an intraocular lens calculation. The invention exhibits an increased tolerance range with regard to an imprecise alignment of the measuring device to the eye.

11 Claims, 5 Drawing Sheets

(56) References Cited

U.S. PATENT DOCUMENTS

| | | |
|---|---|---|
| 2013/0242259 A1 | 9/2013 | Hacker et al. |
| 2013/0301009 A1 | 11/2013 | Hacker et al. |
| 2013/0345807 A1* | 12/2013 | Olsen .......................... 623/6.11 |
| 2014/0092363 A1* | 4/2014 | Volkwardt et al. ............ 351/246 |

OTHER PUBLICATIONS

Haag-Streit AG, "Biometry Connected . . . ", Jun. 2010, 3 pages.

German Search Report for German Application No. DE 10 2012 016 379.7, dated Oct. 30, 2014, 8 pages.

* cited by examiner

METHOD FOR MEASURING AN EYE

FIELD OF THE INVENTION

The present invention relates to a method for measuring the axial length of an eye, wherein the distance of the front of the cornea from the retina is measured using optical coherence tomography (OCT).

BACKGROUND OF THE INVENTION

The preoperative selection of intraocular lenses for cataract treatment constitutes an important application. The most important length measurement for this purpose is the axial length of the eye from the front of the cornea to the retina. According to the prior art, said length is measured preferably with non-contact, optical interferometric methods which are known under the terms PCI (partial coherence interferometry) or OCT (optical coherence tomography). With these methods, structural transitions can be displayed as one-dimensional depth profiles (A-scans) or two-dimensional depth cross sections (B-scans), wherein specular reflections at the optical boundary layers and/or light which is scattered to the various media of the eye are detected.

It is important for both measurement methods that the measurement is taken along an axially oriented axis which corresponds to the visual axis. Otherwise, errors may occur during the selection of the IOL which result in significant defective vision of the patient after implantation of the IOL.

In order to ensure great accuracy of the measurement along the visual axis, the patient, according to the prior art, is provided with a fixation light from the optical measuring device during measurement, onto which the patient fixates the eye. Thus, the visual axis of the eye is aligned with the main measuring axis of the device (device axis) which also corresponds to the z-axis of the coordinate system of the measuring device. This can be found in the literature [1]. Once the device axis is aligned with the visual axis, cornea and retina are, in most cases, positioned sufficiently perpendicular to the main measuring axis, and so the measuring beams reflected from cornea and retina are easily detectable by the measuring device.

According to a first method described in the literature [2], the axis length is measured using partial coherence interferometry with the double-beam method. Two beams with different optical path lengths impinge on the eye and are specularly reflected on the front of the cornea and the retina, resulting in interference. The signals at different optical path lengths are indicative of the eye length. Since a usable signal is only generated when a specular reflection is present from both cornea and retina, this method is advantageous because cornea and retina are approximately perpendicular to the measuring beam, and thus perpendicular to the device axis, for generating a cornea/retina distance signal. Experimentally, it has been shown that under these measurement conditions, which lead to a usable distance signal, the device axis/measuring axis is, in good approximation, identical with the visual axis, and the distance measured along the device axis corresponds to the axial length which is determinative for calculating the IOL. This measurement method quasi-inherently ensures that in case of too great a deviation of the visual axis from the device axis, no incorrect measurement of the eye length is obtained and used for calculating the IOL.

However, it is disadvantageous that, for the duration of the measurement time, the patient must summon a minimum of cooperation for the fixation. If this is not the case, no or very few, and thus statistically fairly unreliable, measurements can be determined for the axial eye length.

It is further disadvantageous that measurements for B-scans or the measuring of the anterior chamber depth are difficult to realize because during such measurements, either cornea or lens show no specular reflection which is also detectable by the device due to the tilted position of the measuring beam with regard to the boundary layers. Thus, newer methods which promise increased reliability regarding the selection of the intraocular lenses and require the measuring of anterior chamber depth, lens thickness, or lens radii are not possible or only possible with difficulty.

According to a second method described in the literature [3], the measurement of intraocular distances takes place using one or more so-called B-scans which are obtained using optical coherence tomography. This allows for the resolution of the front face of the cornea and the retina as well as further tissue structures. For example, cornea thickness, anterior chamber depth, and/or lens thickness can be determined.

For example, the basic principle of the OCT method described in U.S. Pat. No. 5,321,501 A is based on white light interferometry and compares the travel time of a signal using an interferometer (most commonly a Michelson or Mach-Zehnder interferometer). The arm with known optical path length is used as object-external reference for the measurement arm. The interference of the signals from both arms yields a pattern which allows for the determination of the relative optical path length within an A-scan (single depth signal). In one-dimensional scanning grid methods, the beam is then guided transversally in one or two directions, allowing for the recording of a two-dimensional B-scan or a three-dimensional tomogram. This results in a sufficient number of signals even in the B-scan because with this method both specular reflections and scattering in the object are detected.

However, unlike the double-beam method, such methods do not ensure through the measurement principle itself that the axis length (axial length of the eye), which is important for calculating the intraocular lenses, is measured along the correct axis (visual axis). That is because a recording and a signal are possible even if the measuring beam does not impinge perpendicularly on the front face of the cornea and/or is not aligned along the visual axis. The measurement along the device axis results thus in an A-scan which, seen individually, shows no discernible defect, even if it is not measured along the visual axis due to lack of fixation. However, deducting the axis length from measuring along the device axis would generally result in incorrect, systematically shortened measurements because the A-scan, due to poor alignment of the measuring device to the visual axis, eye movement, and/or lack of fixation, measures laterally too far off the visual axis which, in a typically convex eye, results in a shortening of the distance cornea/retina.

In general, such B-scans pose the problem of the lateral attribution of the B-scans in terms of the eye. Due to the temporal duration of one or more B-scans, the eye is not always well fixated during the recording of the B-scans. If said eye movement is not taken into consideration, one B-scan and the intraocular distances, evaluable in such a B-scan, are laterally offset in terms of the eye and thus incorrectly attributed.

Therefore, it is not ensured that the A-scan along the device axis and/or the A-scan which runs within a B-scan along the device axis effectively measures the eye length. Moreover, even with exact alignment, only a few A-scans—only those along the device axis—can be used for calculating the axial length, and so the measured axial length is fraught with a relatively high statistical uncertainty.

LITERATURE

[1] ISO/CD 19980, "Ophthalmic instruments-Corneal topographers." 2009

[2] W. Haig is, "Optical Coherence Biometry," in Modern Cataract Surgery, T. Kohnen, Ed. Basel: Karger Publishers, 2002, pp. 119-1 30

[3] Haag-Streit AG, "Biometry Connected . . . " June-2010

SUMMARY OF THE INVENTION

The present invention addresses the problem of providing a method for measuring an eye, particularly for determining its axis length, corneal thickness, anterior chamber depth, and lens thickness, which allows for the reliable determination of correct, i.e. motion artifact-free, axial eye lengths for the correct selection of intraocular lenses even from B-scans of an OCT measurement or A-scans which are positioned away from the visual axis. A further problem addressed is that of reducing the necessary requirements regarding alignment, resulting in a significant simplification of the measurement process, particularly in case of less cooperative patients. A third problem addressed is that of being able to correct the measured lengths, but at least the axis length.

According to the invention, the problem is solved with the method, according to the invention, for measuring the axial length of an eye through measuring the distance of the front of the cornea from the retina using OCT while measuring or controlling the alignment of the measuring device to the eye in that the topography of the front of the cornea is measured or made available, wherein the calculation of an axial length of the eye is based on an A-scan of the OCT while taking into account a corneal topography registered to the A-scans, and the thus calculated axial length for the intraocular lens calculation is output.

According to the method, the distance of the front of the cornea from the retina is measured using OCT while measuring/controlling the alignment of the measuring device to the eye.

Furthermore, the topography of the cornea is also measured while measuring or controlling the alignment of the measuring device and the eye. In a further step, an axial eye length is calculated for each of a plurality of A-scans from the alignment of the eye and the corneal topography while taking into account the deviation of the A-scans. From said axial lengths, a resulting eye length is thus obtained and output. Said resulting eye length is subsequently used for determining the IOL.

Embodiments of the invention provide a method for measuring an eye which exhibits an increased tolerance range with regard to an imprecise alignment of the measuring device to the eye. The proposed method for verifying a correct alignment can be integrated in various types of measuring devices.

BRIEF DESCRIPTION OF THE DRAWINGS

In the following, the invention is further described in terms of embodiments.

DETAILED DESCRIPTION OF THE DRAWINGS

According to the invention, the method for measuring the axial length of an eye through measuring the distance of the front of the cornea from the retina using OCT while measuring or controlling the alignment of the measuring device to the eye measures or makes available the topography of the front of the cornea, wherein the calculation of an axial length of the eye is based on an A-scan of the OCT while taking into account a corneal topography which is registered to the A-scans. The thus calculated axial length for the intraocular lens calculation is output.

Figure 1:
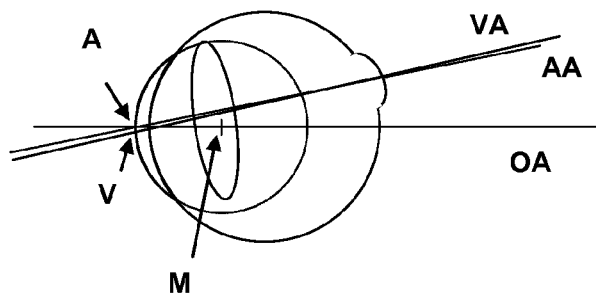
FIG. 1 is a schematic eye with relevant intraocular distances.

FIG. 1 depicts a schematic eye with front and back of a cornea, natural lens, and retina. The cornea is typically characterized by the apex A of the cornea, the point of the greatest curvature of the front of the cornea, and the center of curvature M of the circle which most likely describes the front of the cornea at the point of the apex. Jointly, both define the optical axis of the eye OA. Typically, the point of sharpest vision located at the fovea centralis is now not on the optical axis OA, but lies slightly away from it, and so the visual axis VA is not identical with the optical axis OA of the eye when the eye is aligned with an external fixation axis, but instead slightly tilted with regard to said optical axis. In many cases, the intersection point of the visual axis with the cornea, the so-called visual vertex V, is not identical with the apex A of the cornea. As a rule, the visual axis VA does not have to sit exactly perpendicular to the visual vertex on the cornea. Thus, the visual vertex of the cornea is, strictly speaking, also not identical with the vertex of the cornea, the point at which the cornea surface is positioned perpendicular to the device axis.

For determining the relevant axial eye length for the selection of intraocular lenses using the so-called IOL formula, the axial length along the visual axis VA is hereto determinative.

As mentioned above, it has been experimentally shown that—with sufficient fixation on a fixation light which is offered along the device axis—the axial axis length, relevant for the IOL calculation, can be measured correctly along the device axis with the interferometric double-beam methods. Since this method of measurement detects particularly specular reflections, it follows that the device axis, at the time of fixation, sits sufficiently perpendicular on the cornea in order to still be able to detect the specular reflection of a measuring beam which illuminates the cornea along the device axis. Thus, the measurement is taken along the device axis during fixation practically on the vertex of the cornea.

In this respect, there is effectively only one difference to be neglected with regard to obtaining the axial length relevant for the IOL calculation, i.e., whether the device axis is aligned with the vertex of the cornea or the visual vertex. In the following, there will thus be no difference between denotation of the vertex of the cornea and the visual vertex, it will simply be referred to as vertex. In case of doubt, reference may be made to one or the other vertex with regard to the obtaining of the axial length for the IOL calculation.

Figure 2:
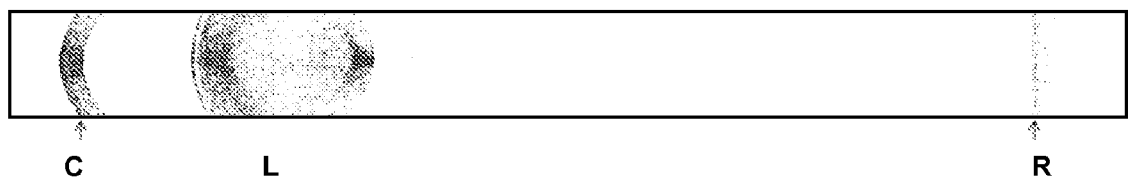
FIG. 2 depicts the signal curve of a B-scan of an eye.

FIG. 2 shows the signal curve of a B-scan of an OCT scan which provides a cross section of the anterior chamber and simultaneously covers the entire eye in its depth. Depicted from left to right are the cornea C, the crystalline lens L, and the retina R. The signal curve of the B-scan infers that the retina appears in the same depth, i.e., the retina R shows absolutely no curvature. With this measurement, the perpendicular, median A-scan in the B-scan corresponds to a scan along the device axis and/or fixation light axis, and therefore the axial length, with sufficient fixation and alignment of the measuring device to the eye, is constituted by this A-scan.

Figure 3:
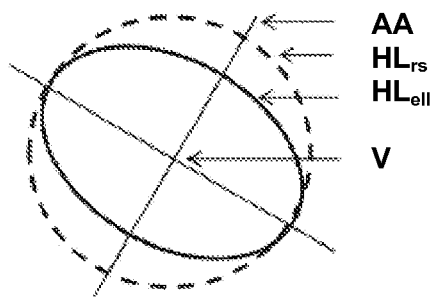
FIG. 3 is a schematic diagram of an anisotropic deformation of a convex, rotationally symmetric front face of a cornea.

However, as shown in FIG. 3, this is generally not the case. Using a contour line, FIG. 3 outlines the form of the cornea surface as seen from the front. In a first-order approximation, the cornea is a spherical surface which is described through a radius of curvature and characterized by a circular, rotationally symmetric contour line (broken line $HL_{rs}$) around the vertex V. In a second-order approximation, the cornea shows an astigmatism in significantly many people, whereby the surface of the cornea can be described through a torus with 2 different radii of curvature in 2 planes which are perpendicular to one another. In this case, the contour lines are elliptic (solid line $HL_{eII}$). Line AA depicts the corresponding axis which defines the astigmatism, wherein the orthogonally depicted axis can also be defined.

If a B-scan through the eye is executed, it depends on the position of the B-scan to the vertex which cross section it measures through the cornea. With correct fixation, the B-scan goes through the vertex because the visual axis corresponds to the device axis. However, due to eye movement, or lack of fixation or alignment of the measuring device to the eye at the time of measurement, this is not generally the case.

It becomes clear that many B-scans measure a distance from the cornea to the retina but very few B-scans will cover the vertex and thus, even fewer A-scans will effectively measure the axial length from vertex to retina from B-scans. Said axial length, however, is relevant for calculating intraocular lenses.

It also becomes clear that B-scans and/or A-scans indicate too short a distance from the front of the cornea to the retina than effectively exists between vertex and retina.

Figure 4:
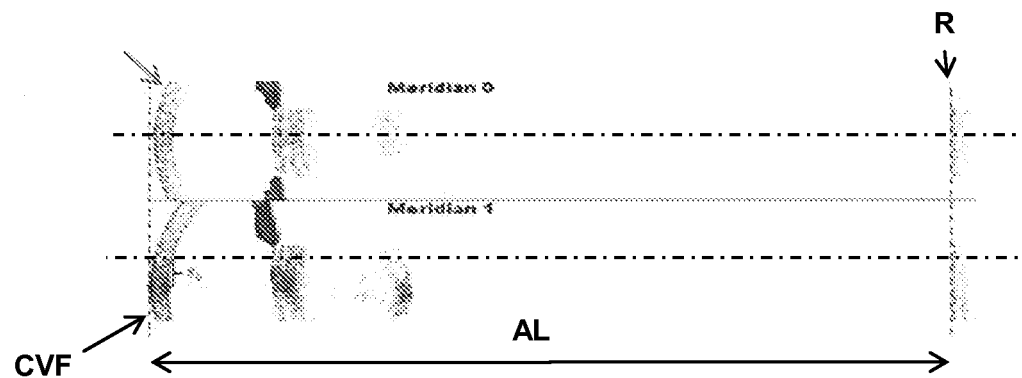
FIG. 4 depicts signal curves of a B-scan pair of an eye with only one correctly aligned B-scan, the most anterior point of the front face of the cornea thus lying on the measuring axis.

In the following, this shall be clarified once more. FIG. 4 shows the signal curves of a B-scan pair for an eye with only one B-scan (Meridian 1) in the scan plane passes through the vertex of the cornea. However, the device axis GA is, once again, not exactly aligned to the visual axis and a correct one can only be detected by detecting the maximum distance of the front face of the cornea (CVF) to the retina in the B-scan. All other cornea/retina distances are systematically too short for a correct axis length AL. However, in the second B-scan (Meridian 0), the most general and frequent case, the scan plane does not comprise the vertex of the cornea, and in such case, even the maximum cornea/retina distance in the B-scan is too short for the correct axial length AL. In order to solve the above outlined problem of axial lengths measured as too short and the small number of A-scans which reproduce the axial length, the following solution, according to the invention, is proposed:

Initially, a vertex point, according to U.S. Pat. No. 7,452, 077, is determined from 2 B-scans, the scan planes of which intersect.

Figure 5:
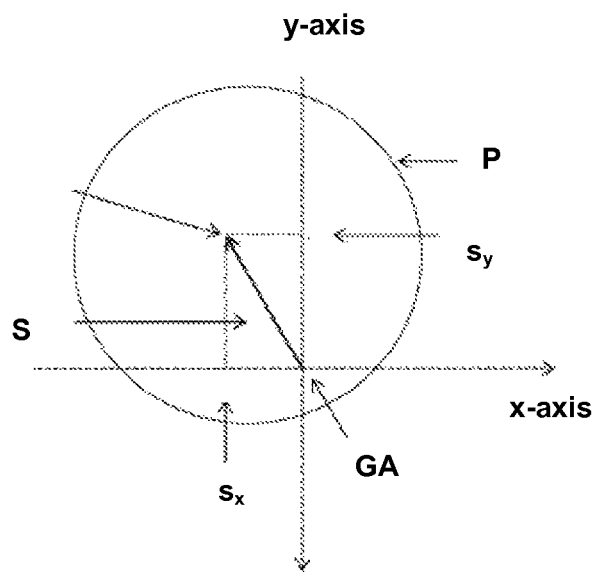
FIG. 5 is a diagram for determining the actual vertex and the lateral distance to device axis and/or scan plane.

FIG. 5 schematically shows the position of an OCT B-scan pair on an image of the eye which is indicated with the pupil P, wherein the scan planes of the B-scans are perpendicular to one another. If the measuring of the B-scan pair is executed very quickly, an eye movement during the scans can be disregarded. However, it cannot be ensured that the patient, at the time of the measurement, is sufficiently fixated and the device is correctly aligned to the eye. Thus, the vertex V does generally not lie on the device axis GA, which is typically constituted through the intersection position of the B-scan pair.

However, the vertex V can be calculated by approximation from the B-scans by determining the position of the most anterior point on the front face of the cornea for every B-scan.

In an example embodiment, this is accomplished through fitting a function to the front face of the cornea and calculating its frontmost point for each of the B-scans. This function, for example, can be a parabola. Consequently, the most anterior point is the vertex. Said fitting, for example, can be effected in accordance with the description of DE 10 2010 051 281 A1. If the first B-scan runs along the x-axis, the vertex equals the position $s_x$. If the second B-scan runs perpendicularly, i.e., along the y-axis, the vertex equals the position $s_y$.

If the position of the vertex V is known, the deviation S from the vertex can also be determined for every A-scan of the B-scan pair. In particular, the deviation of the device axis from the vertex in the coordinate system of the vertex is constituted by coordinate transformation. For example, in case of a shift of the origin of ordinates, while maintaining the x-y-axis direction, the position of the device axis is constituted by $(-s_x, -s_y)$. In summary, a vertex—for example as the most anterior point—is determined from the B-scan pair, and the position/deviation of an A-scan relative to the vertex is constituted by the relative position of the A-scan to the device axis—as controlled by the scan movement, and the relative position of the device axis to said vertex.

The determination of the vertex such described is very well suited for rotationally symmetrical bodies, for example, a spherical cornea. However, the further the B-scan plane rotates out or deviates from the astigmatism axes, this applies decreasingly to toric corneas. Therefore, it is particularly advantageous with known astigmatism axis—as determined by topography—to align the B-scans along said axes by controlling the scanners of the measuring device accordingly, or to select and continue to use from a set of B-scans only those B-scans, which are sufficiently close, e.g. <15 degrees, to said astigmatism axes.

An embodiment of the method according to the invention provides for the calculation of further axial lengths of the eye from further OCT A-scans while taking into account a corneal topography registered to the A-scans, wherein a resulting axial length is obtained from a plurality of such axial lengths and which is output in place of an axial length for the intraocular lens calculation which is defined through only one A-scan.

In order to calculate the axial length for an A-scan from a B-scan with known deviation from the vertex, topographic information, which is also related to the vertex or at least laterally registered with regard to the A-scan, is used.

In this context, topographic information are measurements which are available in the form of a radius of curvature or two radii of curvature and the astigmatism angle or a relief map—high-resolution topography. These are applied to a vertex as measured in conjunction with the topographical measurement.

Furthermore, registration can be effected not only through determining the vertex but, alternatively, with other methods. For example, topography and OCT can be measured simultaneously or within the same timeframe of less than 100 ms while disregarding the eye movement. For example, OCT and/or topography can be each recorded either simultaneously or within the same timeframe in conjunction with an image of iris or sclera and registered to one another using said image of iris or sclera.

Figure 6:
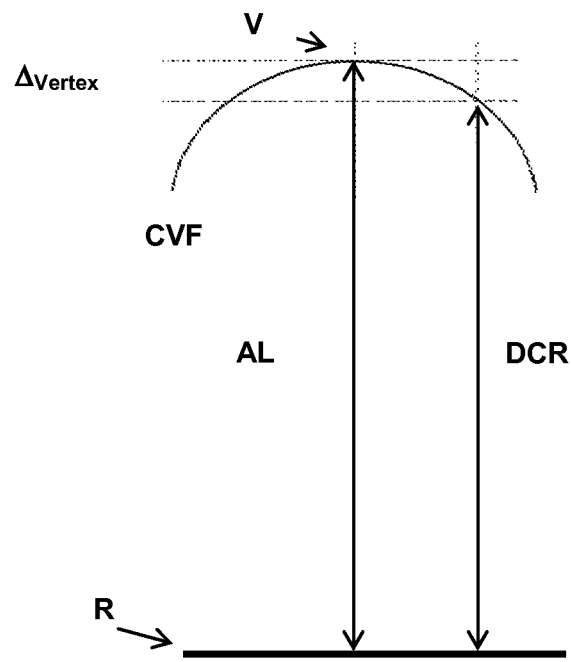
FIG. 6 is a diagram for determining the actual axis length on the vertex using registered, topographic presets.

For further clarification, FIG. 6 shows a diagram for determining the actual axis length AL using registered, topographic information.

For an A-scan with given deviation (s) with regard to the vertex, the corresponding lateral point in the topography with the same deviation (s) from the vertex is determined during the topographical measurement. Its height in the topography is deducted from the height of the vertex point in the topography and thus the height difference $\Delta_{Vertex}$ determined.

The correct axial length AL then results as sum of the OCT distance cornea/retina DCR measured for said A-scan and the height difference $\Delta_{Vertex}$.

This axial length AL is subsequently output by the measuring device as axial length and used for calculating the intraocular lenses.

Of course, with a minor deviation/distance of the device axis from the vertex, while tolerating a certain error, the correction of the axis length can be foregone, and only the deviation must be controlled. It has been found that a deviation S of the device axis GA from the vertex V of no more than 525 µm or no more than 742 µm leads to an error in AL of no more than 25 µm or no more than 50 µm, respectively. However, if greater accuracy is to be achieved, a correction of the axis length, as described above, is sensible.

A further embodiment of the method according to the invention provides for the measurement or control of the alignment for the OCT with the use of a vertex which is defined by a B-scan pair with two intersecting scan planes.

In order to further increase the statistical accuracy, a combined axial eye length AL is determined for a plurality of axial lengths AL, which are determined from a plurality of A-scans in accordance with the above embodiments. In the simplest case, an averaging of the axial lengths can be performed. Furthermore, A-scans with small lateral deviation from the vertex can be weighted higher in the averaging; in doing so, uncertainties and variations of the topographical or OCT measurement in case of greater deviations have less influence on the overall result. Moreover, outliers can be completely excluded from the averaging.

In the following, further embodiments of the method according to the invention are shown:
the B-scan pair is aligned or selected in its scanning position to the astigmatism axes of the front of the cornea;
the topographical measurement is performed with an OCT measuring device, a keratometer, or a Placido topographer, or any other topographical device which is based on pattern projection and observation;
the measurement of the cornea surface is also obtained through measuring the alignment to the eye;
the topography is aligned using a vertex obtained from the topography or by measuring the reflecting light of the fixation light;
the topographical and OCT measurement is performed simultaneously or within the same short timeframe, and so the alignment of the device to the eye during the OCT measurement is determined by the topographical measurement itself; and
the topographical and OCT measurement are each performed simultaneously or within the same short timeframe in conjunction with an image acquisition of iris or sclera for detecting the alignment of the corresponding measuring device to the eye.

Figure 7:
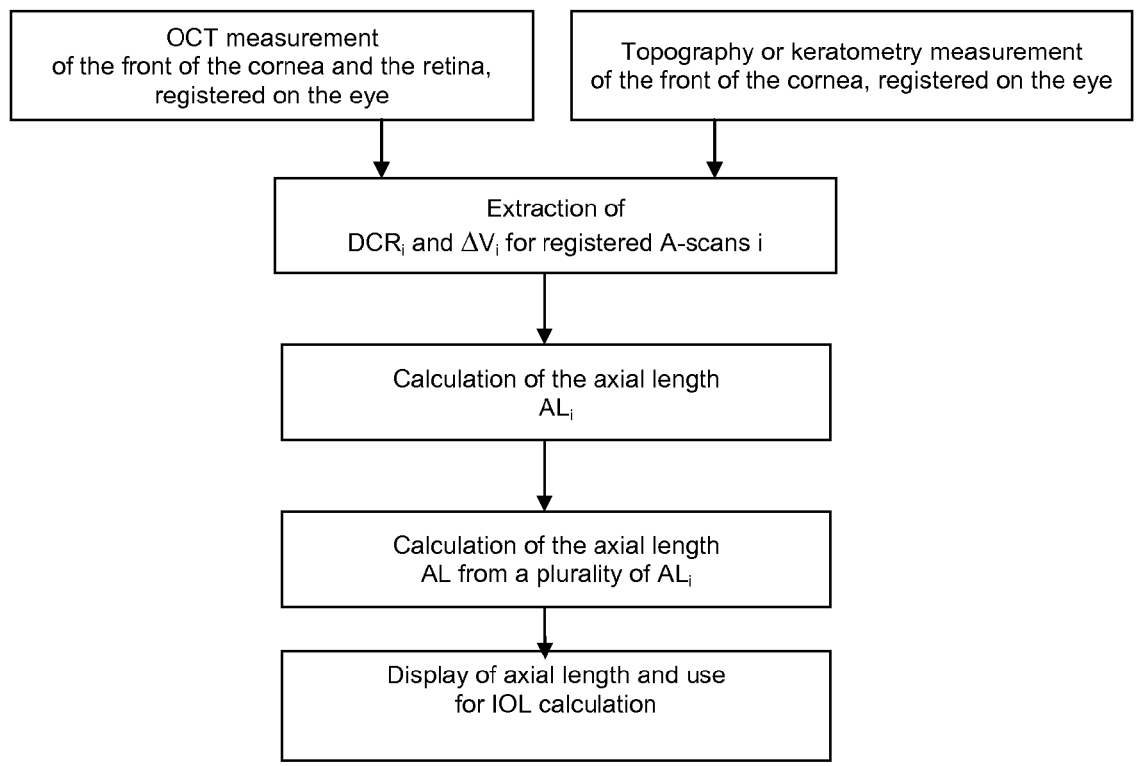
FIG. 7 depicts a sequence of the steps for determining a resulting eye length.

FIG. 7 depicts a sequence for determining the axial eye length: Initially, one or more OCT measurements are performed which are registered in relation to the eye. In addition, a topographical measurement is performed which is also registered in relation to the eye.

Proceeding from both sets of data, one axial length AL, each is determined for one or more A-scans i, using the topographical Information and the cornea/retina distance which is based on the A-scan. In case of a single A-scan, its axial length is output by the measuring device and used for calculating the intraocular lens. In case of a plurality of A-scans, a combined axial length is calculated from the axial lengths and displayed and can thus be used for calculating the IOL.

Figure 8:
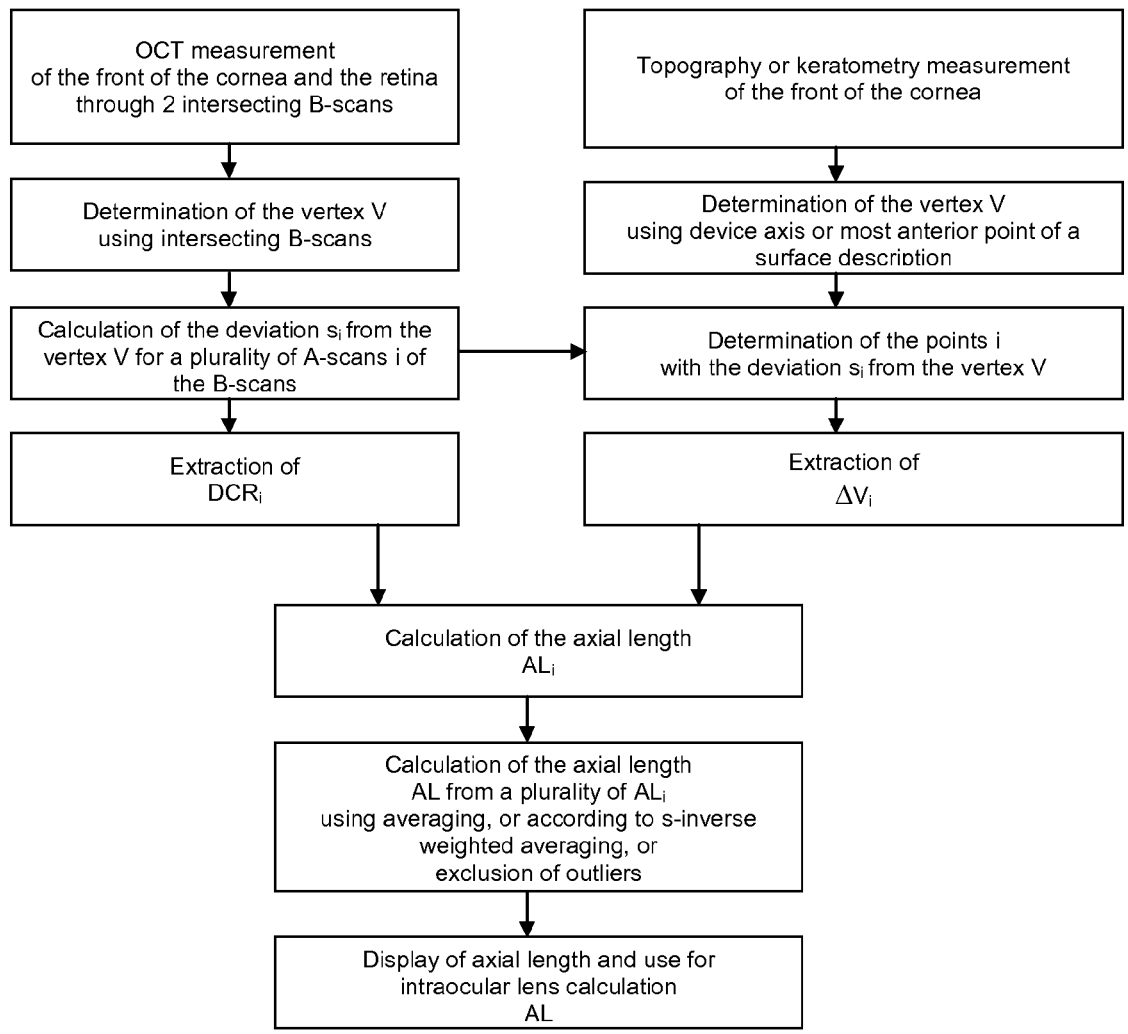
FIG. 8 depicts a further sequence of the steps for determining a resulting eye length.

FIG. 8 depicts a further embodiment for determining the axial eye length. Initially, one or more OCT measurements are performed which are registered in relation to the eye, wherein at least 2 B-scans intersect in their scan planes—for example perpendicular to one another—, wherein a vertex and the deviation of the individual A-scans of the B-scans with regard to said vertex are determined.

In addition, a topographical measurement is performed which is also registered in relation to the eye, wherein, from the topography itself, a vertex is obtained as most anterior point of the topography, or as most anterior point of a Zernike representation of the cornea surface, or as nominal position of the fixation point.

Proceeding from both sets of data, one axial length AL, each is determined for a plurality of A-scans, using the topographical Information and the cornea/retina distance which is based on the A-scan, wherein the A-scan and/or the topographical height of the measuring point is constituted by its deviation with regard to the corresponding vertex.

In case of a single A-scan, its axial length is output by the measuring device and used for calculating the intraocular lens.

In case of a plurality of A-scans, a combined axial length AL is subsequently calculated from the axial lengths and displayed and can thus be used for calculating the IOL; wherein the axial lengths to the individual measuring points are averaged for the combined axial length or averaged weighted inversely to their distance from the vertex.

One aspect has been stated above in conjunction with the determination of the axial length which is also important in a different context:

With regard to the detection of the correct cornea vertex, U.S. Pat. No. 7,452,077 can be improved if known information about the toric surface of the cornea, particularly the alignment of the astigmatism axes and the radii of curvature are taken into account for detecting the vertex.

For such purpose, a toric model of the cornea is constructed from the topography. Assuming that the astigmatism axes do not rotate with regard to the B-scan planes during the B-scan measurements, the most anterior point in the cornea model with regard to the vertex of the cornea model can be determined for every plane parallel to the corresponding scan direction. One set of parallel planes thus constitutes a set of most anterior points, which form a curve with all anterior points of a B-scan parallel to the set of planes. For the registration of a measured B-scan pair with intersecting B-scan planes, the most anterior point is subsequently also determined for every B-scan. Every B-scan is laterally registered such that the most anterior point of the corresponding B-scan lies on the curve of the most anterior points of the set parallel to the corresponding scan plane, and the intersection of the B-scan planes to one another is simultaneously positioned correctly.

The method according to the invention is particularly advantageous because an already existing, exact alignment of the eye to be measured to the optical axis of the measuring device will always be confirmed through comparison of the vertex calculated from the measurements with the intersection of the B-scan pair, regardless of the presets regarding the form of the front face of the cornea, i.e. a correct alignment will always be identified as such.

With the described method, the determined position of the vertex may not only be used for verifying the alignment of device to eye and, if applicable, for the corresponding error compensation.

The combination of keratometry/topography with OCT measurements also allows for the correction of the axis lengths and potentially other measurements as well.

Furthermore, the method according to the invention allows for compiling a 3D eye model, wherein the information regarding the front face of the cornea is obtained from the OCT measurement, or preferably from the keratometry, or, better yet, from the topography.

On the front face of the cornea, the vertex can be determined either from model as point with tangent plane perpendicular to the z-axis or through additional measurements. The visual axis can also be determined explicitly, e.g. through beam tracing starting at the vertex. The length measurements can subsequently be determined from the 3D model on the determined visual axis.

The adjustment of the eye model to the present eye is then effected under certain assumptions, such as description of the boundary layers: Front and back of cornea and lens, through 2D polynomials, torus, ellipsoid, etc.

The solution according to the invention provides a method for measuring an eye, whereby distances are determined using an OCT-based measuring device, and the alignment of the eye to be measured to the optical axis of the measuring device is controlled.

In particular, the method is suitable for measuring eyes and determining their axis lengths, cornea thickness, anterior chamber depth, and lens thickness. According to the invention, the necessary requirements regarding alignment of the measuring device to the eye are reduced, thus significantly simplifying the measurement process even in case of less cooperative patients.

Moreover, a method is provided which exhibits an increased tolerance range with regard to an imprecise alignment of the measuring device to the eye and can thus be used for verifying a correct alignment of various types of measuring devices.

In addition, the proposed method compensates particularly the disadvantage of the single-beam method when compared to the double-beam method.

The invention claimed is:

1. A method for measuring an axial length of an eye, comprising:
   measuring a distance of a front of the cornea from a retina using OCT while measuring or controlling alignment of a measuring device to the eye;
   wherein a corneal topography of the front of the cornea is measured or made available, so that measuring or controlling alignment for the OCT with the use of a corneal vertex is defined by a B-scan pair with two intersecting scan planes;
   calculating the axial length of the eye based on more than one A-scan of the OCT while taking into account the corneal topography registered to the A-scans;
   obtaining a resulting axial length from a plurality of such axial lengths; and
   outputting the thus calculated axial length for intraocular lens calculation.

2. The method according to claim 1, further comprising calculating further axial lengths of the eye from further OCT A-scans while taking into account the corneal topography registered to the A-scans and outputting the resulting axial length in place of the axial length for the intraocular lens calculation defined through only one A-scan.

3. The method according to claim 1, wherein the B-scan pair is aligned or selected to be aligned to the astigmatism axes of the front of the cornea in a scanning position.

4. The method according to claim 1, further comprising performing the topographical measurement with an OCT measuring device, a keratometer, or a Placido topographer.

5. The method according to claim 1, further comprising performing the topographical measurement with a topographical device which is based on pattern projection and observation.

6. The method according to claim 1, wherein the measurement of the cornea surface is also obtained through measuring the alignment to the eye.

7. The method according to claim 6, further comprising aligning the topography using a corneal vertex obtained from the topography or by measuring reflected light of a fixation light.

8. The method according to claim 1, further comprising performing the corneal topography and OCT measurement simultaneously or within a same short timeframe and wherein alignment of the measuring device to the eye during the OCT measurement is determined by the corneal topography measurement itself.

9. The method according to claim 1, further comprising performing the corneal topography and OCT measurement simultaneously or within a same short timeframe in conjunction with an image acquisition of an iris or a sclera that detects the alignment of the corresponding measuring device to the eye.

10. The method according to claim 2, further comprising performing the corneal topography and OCT measurement simultaneously or within a same short timeframe and wherein alignment of the measuring device to the eye during the OCT measurement is determined by the corneal topography measurement itself.

11. The method according to claim 2, further comprising performing the corneal topography and OCT measurement simultaneously or within a same short timeframe in conjunction with an image acquisition of an iris or a sclera that detects the alignment of the corresponding measuring device to the eye.

* * * * *